United States Patent
Schluter et al.

(10) Patent No.: US 7,065,299 B2
(45) Date of Patent: Jun. 20, 2006

(54) MEDICAL DEVICE HAVING A COMBINATION DATA READER AND INFRARED DATA TRANSCEIVER AND METHOD OF USING SAME

(75) Inventors: Paul Schluter, Whitefish Bay, WI (US); Donald E. Brodnick, Cedarburg, WI (US)

(73) Assignee: GE Medical Systems Information Technologies, Inc., Milwaukee, WI (US)

( * ) Notice: Subject to any disclaimer, the term of this patent is extended or adjusted under 35 U.S.C. 154(b) by 448 days.

(21) Appl. No.: 09/730,255

(22) Filed: Dec. 5, 2000

(65) Prior Publication Data

US 2002/0165436 A1 Nov. 7, 2002

(51) Int. Cl.
*H04B 10/00* (2006.01)
*H04B 10/04* (2006.01)
*H04B 10/12* (2006.01)
*G06K 7/10* (2006.01)

(52) U.S. Cl. ............... 398/135; 398/156; 398/201; 235/462.46; 235/462.44; 235/472.02

(58) Field of Classification Search ............... 398/129, 398/135, 136, 151, 156, 162, 168, 170, 172, 398/182, 201; 128/914; 235/462.45, 462.46, 235/462.44, 472.01, 472.02, 472.03, 462.3, 235/462.15, 462.22, 462.23, 462.35; 340/10.51, 340/539.5, 5.92

See application file for complete search history.

(56) References Cited

U.S. PATENT DOCUMENTS

| | | | | |
|---|---|---|---|---|
| 4,957,348 A | * | 9/1990 | May ..................... | 398/136 |
| 5,040,640 A | * | 8/1991 | Slabinski et al. ......... | 187/380 |
| 5,226,431 A | * | 7/1993 | Bible et al. .............. | 600/509 |
| 5,321,492 A | * | 6/1994 | Detwiler et al. .......... | 356/73 |
| 5,562,621 A | | 10/1996 | Claude et al. | |
| 5,602,380 A | * | 2/1997 | Bishay .................. | 235/462.46 |
| 5,670,944 A | * | 9/1997 | Myllymaki .............. | 340/573.1 |
| 5,946,121 A | * | 8/1999 | Jiang et al. .............. | 398/131 |
| 6,091,530 A | * | 7/2000 | Duckworth .............. | 398/129 |
| 6,102,856 A | | 8/2000 | Groff et al. | |
| 6,248,067 B1 | * | 6/2001 | Causey et al. ........... | 600/365 |
| 6,300,880 B1 | * | 10/2001 | Sitnik ................... | 340/825.25 |
| 6,315,719 B1 | | 11/2001 | Rode et al. | |
| 6,581,838 B1 | * | 6/2003 | Meksavan et al. ........ | 235/462.46 |
| 2001/0006193 A1 | * | 7/2001 | Sojka et al. ............. | 235/472.01 |
| 2002/0072785 A1 | * | 6/2002 | Nelson et al. ........... | 607/60 |

OTHER PUBLICATIONS

Merriam-Webster's Collegiate Dictionary; Tenth Edition; Copyright 2000, Merriam-Webster, Inc.; pp. 12 and 72.*

* cited by examiner

*Primary Examiner*—Jason Chan
*Assistant Examiner*—Nathan Curs
(74) *Attorney, Agent, or Firm*—Andrus, Sceales, Starke & Sawall, LLP

(57) ABSTRACT

An electronic apparatus comprising: a housing; an infrared filter window supported by the housing; and an infrared transceiver mounted in the housing so that infrared light emitted by the infrared transceiver is focused in the vicinity of the infrared window, and radiates from the infrared filter window in an approximately 30 degree illumination cone.

30 Claims, 2 Drawing Sheets

MEDICAL DEVICE HAVING A COMBINATION DATA READER AND INFRARED DATA TRANSCEIVER AND METHOD OF USING SAME

BACKGROUND OF THE INVENTION

The invention relates to electronic devices, and particularly to a combined data reader and infrared data transceiver for use in inputting data to a medical device, and to a method of inputting data to a medical device.

Small handheld, portable electronic devices are used in various applications in today's society, e.g., as music players, radios, personal digital assistants (PDAs), and medical devices, such as, for example, Holter monitors and telemetry monitors. Often, because of physical and electrical limitations, these devices are provided with limited means by which to enter data into the device. For example, in the case of common Holter monitors, only one or two buttons are provided to input data such as patient names, times, dates, and other personal data about the patient. As an alternative to inputting data through any kind of push button data entry mechanism, some of these electronic devices are provided with a built-in infrared data transceiver. Typically, such transceivers communicate with similar devices using protocols established by the Infrared Data Association (IrDA). However, in order to effectively use the infrared data transceiver, it is necessary that any device with which a user of the electronic device wants to communicate also include an infrared data transceiver and be programmed to communicate the same protocol as the electronic device. Unfortunately, not all electronic devices are equipped with infrared data transceivers, and not all infrared data transceivers are programmed to communicate with the same protocol.

SUMMARY OF THE INVENTION

Accordingly, the invention provides an electronic device including a combination infrared data transceiver and data reader. The electronic device is preferably a medical device such as a Holter monitor or telemetry based patient monitor, etc., that includes a housing for the storage of electronic assemblies, an infrared filter window supported by the housing to exclude unwanted ambient light of certain frequencies, an infrared lens to focus the transmission and reception of infrared light, an infrared data (IrDA) transceiver for the transmission and reception of infrared light from another IrDA compatible electronic device, an infrared data reader for the illumination of and the reception of infra-red light from a reflective surface, a processor connected to the infrared data reader and the transceiver, and a software program to decode both infrared light reflected from a data source and infrared light that is received from another electronic device. The window and lens may be the same physical device. The IrDA transceiver and the data reader may be the same physical device.

The invention also provides a method for inputting data into an electronic device having an infrared data transceiver. The method for storing data from a reflective surface into an electronic device includes positioning the infrared data transceiver adjacent a reflective surface, activating the infrared data transceiver to emit infrared light, and detecting infrared light reflected from the reflective surface.

The Holter monitor or telemetry based patient monitor is an IrDA compatible device and is able to communicate and exchange information with other IrDA compatible electronic devices. In addition, the Holter monitor or telemetry based patient monitor is able to decode bar code symbols to store relevant information about a patient, i.e., name, age, sex, and patient identification number to correspond with the physiologic patient data collected from the sensors or transducers attached to the patient.

DETAILED DESCRIPTION OF THE PREFERRED EMBODIMENT

Figures 1, 2:
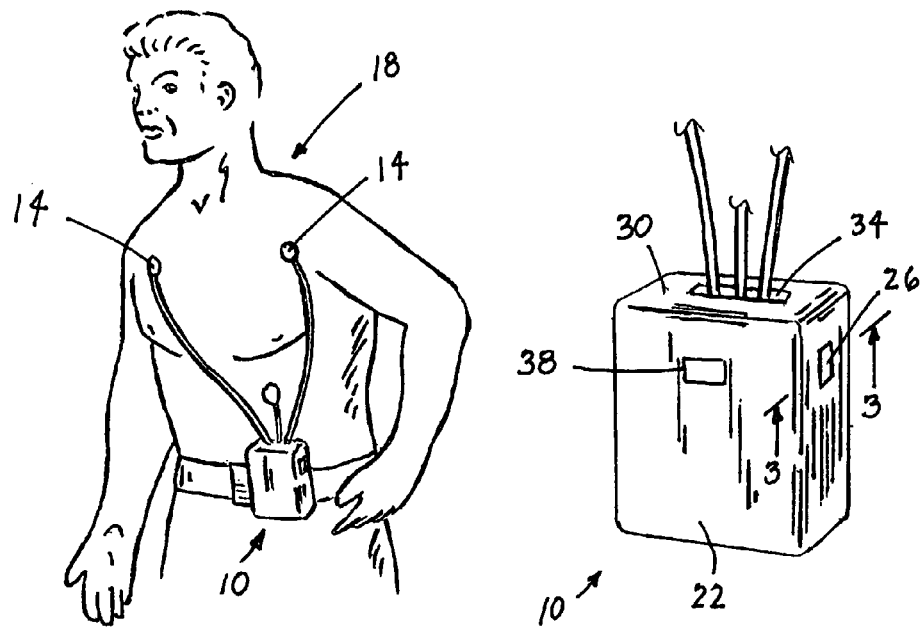
FIG. 1 is a perspective view of an application of a medical device embodying the invention.
FIG. 2 is a perspective view of the medical device.

Before one embodiment of the invention is explained in detail, it is to be understood that the invention is not limited in its application to the details of construction and the arrangements of the components set forth in the following description or illustrated in the drawings. The invention is capable of other embodiments and of being practiced or being carried out in various ways. Also, it is understood that the phraseology and terminology used herein is for the purpose of description and should not be regarded as limiting. The use of "including" and "comprising" and variations thereof herein is meant to encompass the items listed thereafter and equivalents thereof as well as additional items.

Shown in FIG. 1 of the drawings is a medical device such as a Holter monitor or telemetry based patient monitor embodying the invention. The Holter monitor or telemetry based patient monitor 10 is a medical device for the acquisition of physiologic patient data. The Holter monitor or telemetry based patient monitor 10 acquires physiologic patient data via sensors or transducers 14 that are mounted on a patient 18 and placed in a particular arrangement. The Holter monitor or telemetry based patient monitor 10 stores the acquired physiologic patient data until such time as the data is analyzed or transferred to a long term data storage facility.

Figure 3:
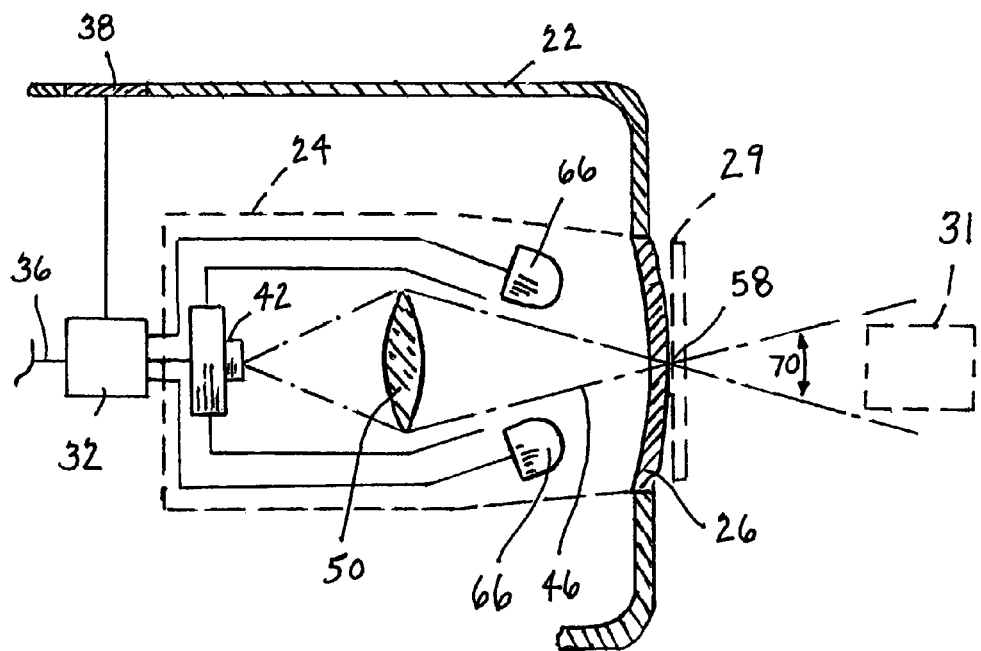
FIG. 3 is an enlarged partial schematic representation of the combination data reader and infrared data transceiver in the medical device taken generally along line 3—3 in FIG. 2.

As shown in FIG. 3, the Holter monitor or telemetry based patient monitor 10 has a housing 22 manufactured from typical medical device materials such as high-impact plastic. The housing 22 supports a combination infrared data transceiver and infrared data reader 24 (hereinafter transceiver/reader 24). Transceiver/reader 24 includes an infrared filter window 26, typically supported by the housing 22. The infrared filter window 26 may be located on any one side of the housing 22 and has an outer surface 62.

The transceiver/reader 24 is electrically connected to and controlled by control circuitry 32 that includes, but is not limited to a processor and software program. The housing 22 supports a connector 34 (as shown in FIG. 2), on any one side of the housing 22, but preferably on the top side 30, for connecting the sensors or transducers 14 to control circuitry 32 via 36 (FIGS. 3 and 4) inside the housing 22. A keypad 38, or any similar mechanism, supported by the housing 22 is also connected to the control circuitry 32 inside the housing 22 for controlling the functions of the Holter monitor or telemetry based patient monitor 10.

Figure 4:
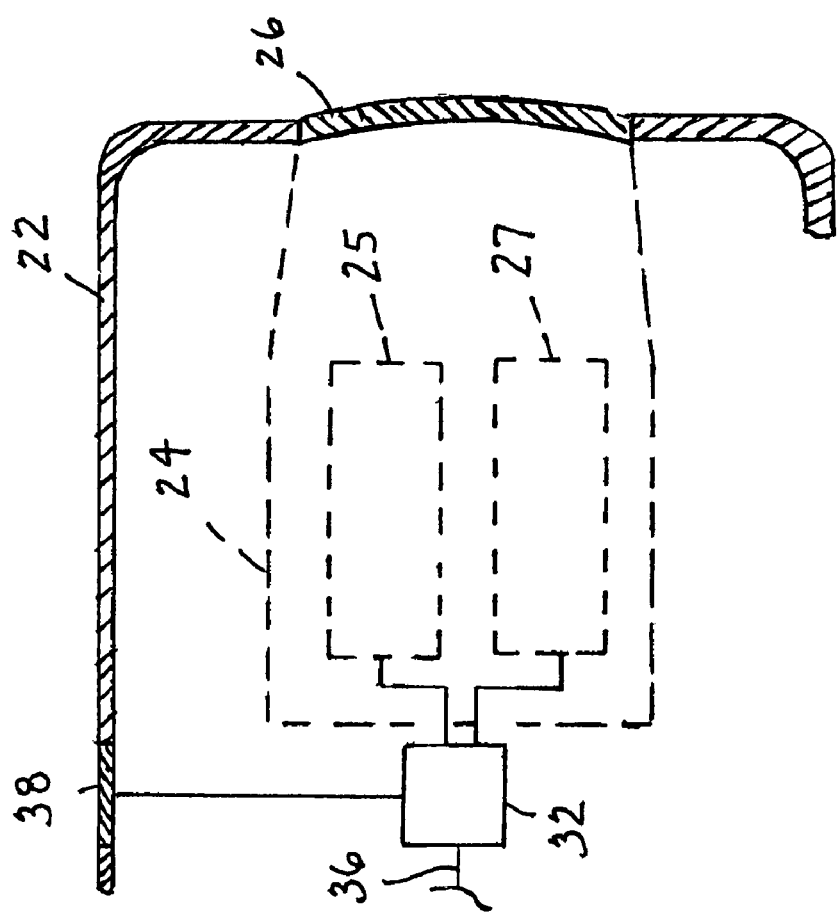
FIG. 4 is a view similar to FIG. 3 showing an alternative construction of the combination data reader and infrared data transceiver.

As shown in FIG. 4, the transceiver/reader 24 includes an infrared data transceiver 25 and an infrared data reader 27. The infrared data transceiver 25 transmits and receives infrared light from other infrared compatible electronic devices (e.g., the IrDA compatible electronic device 31 schematically illustrated in FIG. 3). The infrared data reader 27 illuminates and receives infrared light from a reflective surface (e.g., the reflective surface 29 schematically illustrated in FIG. 3). The infrared data transceiver 25 and the infrared data reader 27 may be separate devices or the same physical device. FIG. 3 illustrates a construction of the transceiver/reader 24 that includes the infrared data transceiver 25 and the infrared data reader 27 as the same physical device.

As shown in FIG. 3, the transceiver/reader 24 includes a light-emitting diode 42 connected to the control circuitry 32, a convex-shaped lens 50 positioned between the light-emitting diode 42 and the infrared filter window 26, and two photodetectors 66 positioned near the infrared filter window 26 and connected to the control circuitry 32.

The transceiver/reader 24 is activated by applying force to the keypad 38, or similar mechanism. The keypad 38, or any similar mechanism, activates the control circuitry 32 which triggers the light-emitting diode 42 to emit an infrared beam of light 46 in the direction of the infrared filter window 26. The infrared beam of light 46 forms an illumination cone of light. The infrared beam of light 46 intersects with the lens 50 positioned normal to the direction of the infrared beam of light 46. The lens 50 focuses the illumination cone of light of the infrared beam of light 46 to an intersection point 58 at outer surface 62 of the infrared filter window 26.

At intersection point 58, the infrared beam of light 46 is focused to a sufficiently small point to read data encoded on a reflective surface 29, e.g., a bar code symbol or other infrared reflective text or code. The data encoded on a reflective surface 29 is reflected in the infrared beam of light 46 through the infrared filter window 26. The reflected infrared beam of light is detected by the photodetectors 66 inside the housing 22. The data in the reflected infrared beam of light that is detected by the photodetectors 66 is decoded by a processor and software program located within the control circuitry 32. The decoded data is stored within the Holter monitor or telemetry based patient monitor 10. In another embodiment (not shown), the keypad 38 is integral with the filter window 26 so that when the filter window 26 is pressed against the reflective surface 29 (i.e., a force is applied to the filter window 26), the transceiver/reader 24 is automatically activated to illuminate, read and decode the data or text embodied in the reflective surface 29.

The transceiver/reader 24 is capable of transmitting data when it is not used to read data on a reflective surface 29. Any data stored within the Holter monitor or telemetry based patient monitor 10 can be transmitted via an infrared beam of light to another IrDA compatible electronic device 31. As shown in FIG. 3, the transceiver/reader 24 includes a light-emitting diode 42 connected to the control circuitry 32, a convex-shaped lens 50 positioned between the light-emitting diode 42 and the infrared filter window 26, and two photodetectors 66 positioned near the infrared filter window 26 and connected to the control circuitry 32. When keypad 38 is activated, the infrared beam of light emitted by light-emitting diode 42 in the direction of the infrared filter window 26, continues outside of the infrared filter window 26 in a path of an illumination cone outside of the infrared filter window 26 at an approximate 30° angle 70. The minimum angle 70 of the illumination cone of the infrared beam of light is 30°. Any IrDA compatible device 31 within the illumination cone may receive data encoded within the infrared beam of light.

Similarly, another IrDA compatible electronic device may transmit data for storage to the Holter monitor or telemetry based patient monitor 10. The photodetectors 66 detect the presence of infrared light through the infrared filter window 26 from another IrDA compatible electronic device emitting a similar 30° illumination cone of light in the direction of the Holter monitor or telemetry based patient monitor 10. The minimum angle of the illumination cone at which the Holter monitor or telemetry based patient monitor 10 can detect data from another IrDA compatible device's infrared beam of light is 30°. The data transmitted in the infrared light from another IrDA compatible electronic device and detected by photodetectors 66 is decoded by the processor and software program located within the control circuitry 32. The decoded data is stored within the Holter monitor or telemetry based patient monitor 10.

Other features and advantages of the invention are set forth in the following claims.

What is claimed is:

1. An electronic apparatus comprising:
    a housing;
    sensing means coupled to the apparatus, wherein the sensing means are configured to provide a set of patient data to the apparatus;
    an infrared filter window supported by the housing; and
    an infrared transceiver mounted in the housing so that a focal point of infrared light emitted by the infrared transceiver to transmit data to another electronic apparatus is focused at the infrared filter window, and radiates from the infrared filter window in an illumination cone, such that the focal point of the infrared light illumination cone is on the outer surface of the infrared filter window.

2. The electronic apparatus of claim 1, wherein the infrared transceiver includes a light emitting diode.

3. The electronic apparatus of claim 1, wherein the infrared transceiver includes a lens supported by the housing.

4. The electronic apparatus of claim 1, wherein the infrared transceiver includes at least one photodetector.

5. The electronic apparatus of claim 1, wherein the apparatus further comprises a processor supported by the housing and electrically connected to the infrared transceiver.

6. The electronic apparatus of claim 5, wherein the apparatus further comprises a software program stored in the processor for decoding both infrared light reflected from a data source and infrared data transmitted from another electronic apparatus, and wherein the data source includes a reflective surface having patient information encoded thereon.

7. The electronic apparatus of claim 1, wherein the apparatus is a Holter monitor.

8. The electronic apparatus of claim 1, and further comprising an infrared data reader mounted in the housing so that infrared light emitted by the data reader to read data encoded on a data source is focused at the infrared filter window.

9. The electronic apparatus of claim 1, and further comprising a combination data reader and infrared data transceiver mounted in the housing so that infrared light emitted by the combination data reader to another electronic apparatus is focused at the infrared filter window, and wherein the combination data reader and infrared data transceiver comprises the infrared transceiver.

10. The electronic apparatus of claim 1, wherein the illumination cone comprises an approximately 30 degree illumination cone.

11. The electronic apparatus of claim 1, wherein the illumination cone comprises an at least approximately 30 degree illumination cone.

12. The electronic apparatus of claim 1, wherein the electronic apparatus comprises a medical device.

13. An electronic apparatus comprising:
a housing;
sensing means coupled to the apparatus, wherein the sensing means are configured to provide a set of patient data to the apparatus;
an infrared filter window supported by the housing;
a combination data reader and infrared data transceiver supported by the housing and configured to read data encoded on a data source and to transmit data to another electronic apparatus, wherein infrared light emitted by the combination data reader and infrared data transceiver to read data and to transmit data includes a common focal point at the infrared filter window;
a processor connected to the combination data reader and infrared data transceiver; and
a software program executed by the processor to decode both infrared light reflected from a data source and infrared data transmitted from another electronic apparatus, such that the common focal point of the infrared light is on the outer surface of the infrared filter window.

14. The electronic apparatus of claim 13 wherein the software program initiates transmission of data via infrared light to another electronic apparatus.

15. The electronic apparatus of claim 13 wherein the combination data reader and infrared data transceiver includes a light emitting diode that emits the infrared light and a lens that focuses the infrared light to a small point at the common focal point in the vicinity of the infrared filter window.

16. The electronic apparatus of claim 15 wherein the lens also creates an illumination cone subtending at least 30 degrees beyond the infrared filter window.

17. The electronic apparatus of claim 13 wherein the combination data reader and infrared data transceiver includes at least one photodetector.

18. The electronic apparatus of claim 13 wherein the data source includes a reflective surface having patient information encoded thereon.

19. The electronic apparatus of claim 16 wherein the combination data reader and infrared data transceiver detects infrared light emitted from another electronic device positioned within the illumination cone.

20. The electronic apparatus of claim 13, wherein the apparatus is a Holter monitor.

21. A method of inputting data into an electronic device having an infrared data transceiver and a filter window, the method comprising the acts of:
positioning the infrared data transceiver adjacent a reflective surface having data encoded thereon;
applying a force to the filter window using the reflective surface to activate the infrared data transceiver to emit infrared light; and
detecting infrared light reflected from the reflective surface.

22. A method as set forth in claim 21 wherein the positioning of the infrared data transceiver is such that the infrared beam of light has a direct line of sight to the reflective surface.

23. A method as set forth in claim 21 wherein the electronic device includes a keypad, and wherein the method further comprises the act of applying a force to the keypad to activate the infrared data transceiver to emit infrared light.

24. A method of inputting data into a medical device, the method comprising:
providing a medical device having
an infrared filter window supported by the housing,
a combination data reader and infrared data transceiver supported by the housing and configured to read data encoded on a reflective surface and to transmit data to another infrared compatible electronic apparatus;
providing a reflective surface having patient information encoded thereon;
emitting infrared light from the combination data reader and infrared data transceiver to read data, the emitted infrared light being focused such that a focal point of the emitted infrared light is at the infrared filter window;
decoding infrared light reflected from the reflective surface to obtain at least some of the patient information; and
emitting infrared light from the combination data reader and infrared data transceiver to transmit data, the focal point of the emitted infrared light is focused at the infrared filter window, such that the focal point of the infrared light emitted for reading data and transmitting data is on the outer surface of the infrared filter window.

25. The method of claim 24 wherein the step of emitting infrared light to transmit data includes radiating the infrared light beyond the infrared filter window in an at least approximately 30 degree illumination cone.

26. The method of claim 25 and further comprising
providing another infrared compatible electronic apparatus; and
decoding infrared data transmitted from the another infrared compatible electronic apparatus positioned substantially within the illumination cone.

27. The method of claim 24 wherein the combination data reader and infrared data transceiver is a single device.

28. The method of claim 24 wherein the combination data reader and infrared data transceiver includes a data reader and a separate infrared data transceiver.

29. The method of claim 24 wherein the patient information includes at least one of a patient name and a patient identification number.

30. The method of claim 24 wherein providing a medical device includes providing one of a Holter monitor and a telemetry based patient monitor.

* * * * *